United States Patent
Swanberg et al.

(10) Patent No.: US 12,201,703 B2
(45) Date of Patent: Jan. 21, 2025

(54) RADIOTHERAPY GEL AND METHOD OF PREPARING THE SAME

(71) Applicant: Vivos, Inc., Richland, WA (US)

(72) Inventors: David Swanberg, Kennewick, WA (US); James Duncan, Richland, WA (US); Darrell Fisher, Richland, WA (US)

(73) Assignee: Vivos, Inc., Richland, WA (US)

( * ) Notice: Subject to any disclaimer, the term of this patent is extended or adjusted under 35 U.S.C. 154(b) by 0 days.

(21) Appl. No.: 18/152,137

(22) Filed: Jan. 9, 2023

(65) Prior Publication Data

US 2023/0263913 A1 Aug. 24, 2023

Related U.S. Application Data

(63) Continuation-in-part of application No. 17/943,311, filed on Sep. 13, 2022, which is a continuation-in-part of application No. 17/740,549, filed on May 10, 2022, which is a continuation-in-part of application No. 16/459,466, filed on Jul. 1, 2019, now Pat. No. 11,478,557.

(60) Provisional application No. 63/299,930, filed on Jan. 15, 2022.

(51) Int. Cl.
*A61K 51/02* (2006.01)
*A61K 51/12* (2006.01)

(52) U.S. Cl.
CPC .......... *A61K 51/02* (2013.01); *A61K 51/1217* (2013.01); *A61K 51/1241* (2013.01)

(58) Field of Classification Search
CPC ............... A61K 51/02; A61K 51/1217; A61K 51/1241; A61K 51/1213
See application file for complete search history.

(56) References Cited

U.S. PATENT DOCUMENTS

| 6,296,831 | B1 | 10/2001 | Weller |
| 6,841,617 | B2 | 1/2005 | Jeong |
| 7,087,244 | B2 | 8/2006 | Jeong |
| 2003/0144570 | A1 * | 7/2003 | Hunter ................. A61L 31/18 600/1 |
| 2004/0228794 | A1 | 11/2004 | Weller |
| 2021/0060183 | A1 * | 3/2021 | Delaney, Jr. ........... A61L 27/52 |

OTHER PUBLICATIONS

Baumann, A., Tureck, E., Prabhu, S., Dickmann, L., Sims, J., Pharmacokinelics, metabolism and distribution Jf PEGs and PEGylated proteins: quo vadis?, Drug Discov. Today, vol. 19, 1623-1631, 2014.
Erbetta, CDC, Alves RJ., Resende, JM., Freitas RFS., Sousa, RG., Synthesis and Characterization of Poly D,L-laclide-co-glycolide) Copolymer. Journal of Biomaterials and Nanbiotechnology, vol. 3, 2 0 8-225, 2012.
Servais, KJ., Evaluation of biodegradable thermogel polymer for intraocular delivery of a cyclosporine A to prevent posterior capsule opacification, PhD Thesis, The Ohio State University, 2017.
Laycock, B., Nikolic, M., Colwell, JM., Gauthier, E., Halley, P., Bottle, S., George G., Lifetime Prediction of Biodegradable Polymers, Prag. Polym. Sci, vol. 71, 144-189, 2017.
Lee, SS., Hughes, P., Ross, AD., Robinson, MR., Biodegradable implants for sustained drug release in the eye. Pharm. Res., vol. 27, 2043-2053, 2010.
Manickavasagam; E., Oyewumi, MO., Critical assessment of implantable drug delivery devices in glaucoma management. J_ Drug Deliv., vol. 2013, 1-12, 2013.
Souza, MGM., Fialho, SL., Souza, PAF, Fulgencio, GO, Da Silve, GR, Silva-Cunha, A., Tacrolimus-loaded PLGA implants: In vivo release and ocular toxicity. Curr. Eye Res. vol. 39, 99-102, 2014.
Stevanovic, M., Maksin, T., Petkovic, J., Filipic, M., Uskokovic, D., An Innovative, Quick and Convenient Labeling Method for the Investigation of Pharmacological Behavior and the Metabolism of Poly(DL-lactide-coglycolide) Nanospheres, Nanotechnology, vol. 20, 1-12, 2009a.
Webster, R., Didier, E., Harris, P., Siegel, N., Stadler, J., Tilbury, L., Smith, D., PEGylated proteins: evaluation of their safety in the absence of definitive metabolism studies. Drug Metab. Dispos. vol. 35, 9-16.2007.

* cited by examiner

*Primary Examiner* — Robert S Cabral
(74) *Attorney, Agent, or Firm* — Indiano Law Group, LLC; E. Victor Indiano; C. John Brannon

(57) ABSTRACT

A radioactive thermogel suspension, including a thermogel and a plurality of insoluble radioactive isotope phosphate particles, such as yttrium phosphate, suspended in the thermogel. The thermogel is PLGA-g-PEG. The thermogel contains less than 65 ppm stannous octanoate. The plurality of radioactive yttrium phosphate particles are between 0.03 μm and 10 μm in diameter. The plurality of radioactive yttrium phosphate particles are generally spherical. The $YPO_4$ particle concentration is in the range of 3 mg/ml to 100 mg/ml.

17 Claims, 1 Drawing Sheet

RADIOTHERAPY GEL AND METHOD OF PREPARING THE SAME

CROSS-REFERENCE TO RELATED APPLICATIONS

This patent application claims priority to co-pending U.S. patent application Ser. No. 17/943,311, filed on Sep. 13, 2022, which is a continuation-in-part of U.S. patent application Ser. No. 17/740,549, filed on May 10, 2022, which is a continuation-in-part of then U.S. patent application Ser. No. 16/459,466, filed on Jul. 1, 2019; this patent also claims priority to U.S. Provisional Patent Application Ser. No. 63/299,930, filed on Jan. 15, 2022.

TECHNICAL FIELD

The present novel technology relates generally to the field of radio-medicine and, more particularly, to a gel and method of preparing the same.

BACKGROUND OF THE INVENTION

One common approach to the treatment of patients with certain kinds of cancer, such as liver cancer, is to introduce radioactive particles into the patient's circulatory system, wherein the radioactive particles are targeted to the site of the cancer. Specifically, measured amounts of radioactive isotopes are injected into the patient such that they accumulate at the site of the cancer. The lodged particles thus generate a predetermined field of radiation within or proximate to the location of a cancerous tumor. The particular radioactive isotope is typically selected according to the type of radiation emitted and its half-life, such that the radiation has enough range to be destructive to the tumor and proximal tumor margins but does only minimal damage to adjacent healthy tissues and organs and also such that the emission of radiation lasts for only a short, predetermined duration.

One commonly-used radioisotope is yttrium-90, since radioactive yttrium-90 emits 100 percent beta radiation and has a short half-life of 2.67 days. The yttrium-90 is typically incorporated in glass or resin microspheres which are suspended in a liquid medium and introduced via intra-arterial injection. However, the glass or resin formulations and mode of administration resulted in: a) difficulties in achieving a homogeneous distribution of particles within the tumor (and thus not treating the patient with a known and controlled radiation dosage); and b) difficulties in concentrating and sequestering all of the radioisotope at the tumor site allowing significant amounts of the particles to migrate away from the tumor site and deliver radiation to normal healthy tissues.

Various means have been employed to incorporate the treatment radioisotopes in microspheres, such as those made of resin or crystalline ceramic cores with radioactive materials coated thereunto. However, whenever a microsphere comprises a core material having an external surface coating which contains the radioactive isotope there is a risk that the radioactive coating may separate from the underlying microsphere core. Any mechanical breakage of the coating can release unwanted radioactivity to other parts of the patient's body, which is highly undesirable. Further disadvantages are presented by the special handling and precautions that are necessary to coat a radioactive isotope onto a crystalline ceramic core, or to label ion exchange resin.

In still another application, microspheres have been prepared comprising a ceramic material and having a radioactive isotope incorporated into the ceramic material. While the inadvertent release of radioactive isotopes from a radioactive coating into other parts of the human body is reduced or eliminated by incorporating the radioisotopes into ceramic spheres, the latter product form is nevertheless not without its disadvantages. Processing of these ceramic particles is dangerous because potentially volatile radioactivity must be added to ceramic melts and the microspheres must be produced and sized while radioactive. Such processing steps increase the likelihood of accidental exposure of personnel and risk radioactive contamination of facilities.

Some of these drawbacks have been overcome by incorporating stable $^{89}Y$ in oxide form into glass microspheres and subsequently exposing them to neutron radiation to activate the $^{89}Y$ to $^{90}Y$. The microspheres are then injected into the patient hepatic artery, where they may lodge in liver tumor capillaries. Microspheres may end up in normal liver or be transported elsewhere in the body. It is difficult to track and accurately assess where all of the administered microspheres deposit.

Thus, there remains a need for a better or optimized treatment that is useful in the treatment of cancer or tumor bearing tissue, but which will not release a radioactive coating or isotope, or migrate into other parts of the body of the patient after administration, will not require technicians to directly handle radioactive materials during the formation of the microspheres, which have a size and density which will permit the particles to be suspended in a fluid suitable for direct injection into tumor tissues, and which may be readily traced to assure accurate delivery of the radiation treatment to the desired tumor site. The present invention addresses this need.

BRIEF DESCRIPTION OF THE FIGURES

The foregoing and other features and advantages of the present invention will become more readily appreciated as the same become better understood by reference to the following detailed description of the preferred embodiment of the invention when taken in conjunction with the accompanying drawings, wherein.

Figure 1:
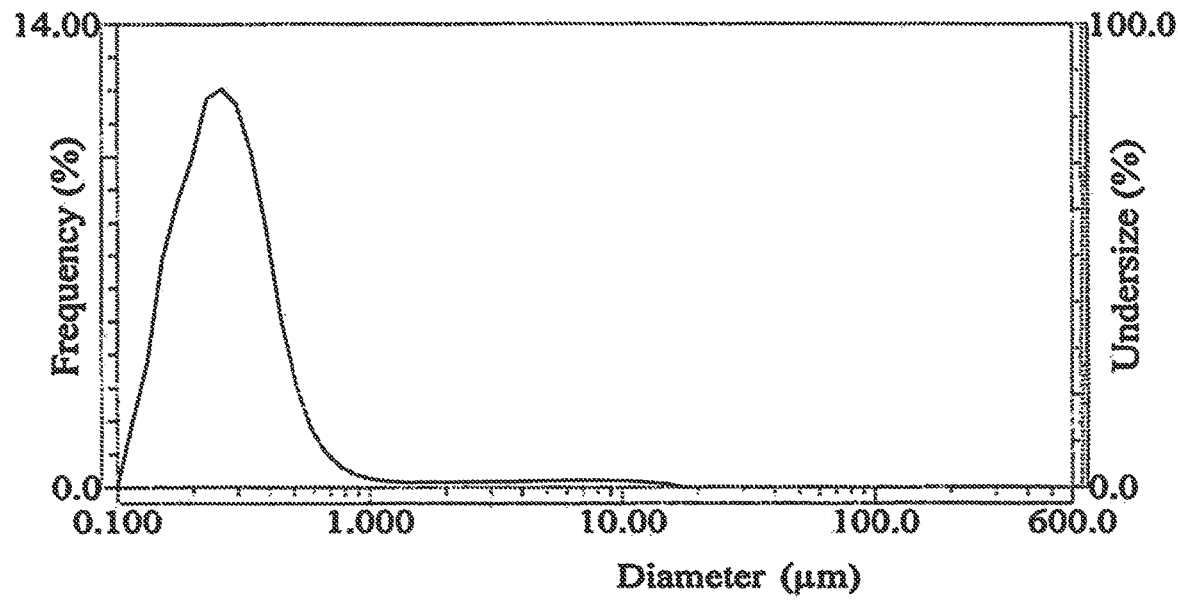
FIG. 1 illustrates particle size determined through the claimed process with pH of 7.35 yielding particle median size of 0.2450 um.
Figure 2:
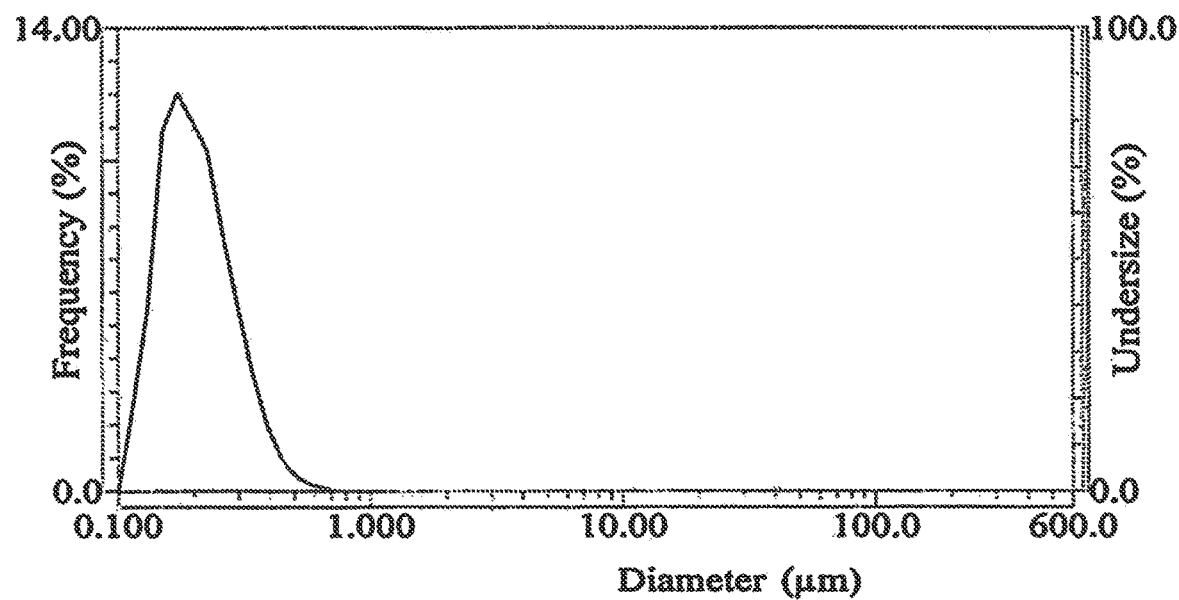
FIG. 2 illustrates an yttrium particle suspension having a pH 7.4 and median particle size of 0.1844 um, providing effectiveness for tumor interstitial, extracellular space applications.

The foregoing descriptions of specific embodiments of the present invention have been presented for purposes of illustration and description. They are not intended to be exhaustive or to limit the present invention to the precise forms disclosed, and obviously many modifications and variations are possible in light of the above description and figures. The exemplary embodiment was chosen and described in order to best explain the principles of the present invention and its practical application for purposes of enabling others who are skilled in the art and making of the product to best utilize the present invention and various embodiments with various modifications as are suited to the particular use contemplated.

DETAILED DESCRIPTION

For the purposes of promoting an understanding of the principles of the novel technology and presenting its currently understood best mode of operation, reference will now be made to the embodiments illustrated in the drawings and specific language will be used to describe the same. It will nevertheless be understood that no limitation of the scope of the novel technology is thereby intended, with such alterations and further modifications in the illustrated device and such further applications of the principles of the novel technology as illustrated therein being contemplated as would normally occur to one skilled in the art to which the novel technology relates.

In one embodiment, the present novel technology relates to a method of preparing a radioactive insoluble particle suspension, in this example a radioactive yttrium particle suspension. Yttrium salts such as yttrium chloride, yttrium nitrate, yttrium sulfate, yttrium bromide and combinations thereof are irradiated with neutron radiation to activate the yttrium (convert stable $^{89}Y$ to radioactive $^{90}Y$). This may be done either before or after they are put into a stable suspension as follows.

The yttrium salts are put into solution and subsequently combined with a solution of soluble phosphates salt(s), such as sodium phosphate, lithium phosphate, potassium phosphate, and combinations thereof, and having a stoichiometric excess of phosphate. The resultant admixture is maintained at a pH in the range of 1.5 to 8. The solutions are agitated, typically with continuous stirring and also rapidly heated in a closed vessel to about 150 degrees Celsius and held for from about one to about ten hours to yield a greater than about 99.99% conversion of soluble yttrium to insoluble $YPO_4$ as well as to achieve a desired particle size distribution, typically less than 2 microns in diameter, more typically in the range of 0.03 um to 10 um, still more typically in the range of 0.05 um to 3 um, and yet more typically in the range of 0.1 um to 2 um with a median particle size of about 0.2 um. Through careful control of mixing time, temperature, and concentration of the reactants, a specific, desired particle size distribution and/or particle shape distribution of $YPO_4$ particles suspended may be achieved. Likewise, once the $YPO_4$ particles are formed, the solution may be buffered with saline to achieve neutral pH suitable for direct injection into human or animal tissue.

Typically, the radioactive particle suspension has a mean particle size of less than 2 um. The radioactive particle suspension is typically characterized by at least 90 percent of the total particle volume having generally spherical particles in the range of 0.1 um to 2 um. Typically, the starting concentration of soluble yttrium in the combined solution is in the range of 0.05 to 1.0 mole/liter, more typically in the range of 0.05 to 0.3 mole/liter, and still more typically in the range of 0.08 to 0.3 mole/liter and the stoichiometric excess of phosphate ranges from 10% to 100%. More typically, the starting concentration of soluble yttrium in the combined solution is 0.08 moles/liter and the stoichiometric excess of phosphate is in the range of 5% to 100%, more typically about 10%, and still more typically about 25%.

In other embodiments, the radioactive metal cation is selected from members of the Lanthanide series, such as Ce, Sm, Ho, Yb, Lu, and the like, and combinations thereof. In still other embodiments, the radioactive cation is selected from members of the metals and transition metals, such as Ga, In, Sn, Pb, Cu, Y, Sc, and the like and combinations thereof to yield insoluble or sparingly soluble transition metal phosphate(s). In yet other embodiments, the radioactive cation is selected from members of the alkali metals/alkali earth metals, such as Cs, Ra, Ca, Sr, Ba, and the like and combinations thereof, although these may be combined with insoluble inorganic compounds such as zeolites, as their phosphates may not be sufficiently insoluble. In still other embodiments, the radioactive cation is selected from members of the Actinide series, such as $^{225}Ac$, and in yet other embodiments, the radioactive cation is selected from members of the metals, transition metals, alkali metals, alkali earth metals, the Lanthanides, the Actinides, and combinations thereof. In some embodiments, the radioactive cation is selected from the members of the group including Y, La, Ce, Pr, Pm, Sm, Gd, Tb, Ho, Yb, Ce, Pb, Lu, Ac, Ca, Sr, Ba, Ra, Cs, Cu, Tc, Pd, Sn, Re, Au, and combinations thereof, while the phosphate functional group may include one or more radioisotopes of phosphorous, such as $^{32}P$ and $^{33}P$ (with $^{31}P$ being the stable isotope). In some cases, the functional group may include an iodide wherein the I is a radioisotope, such as $^{123}I$, $^{124}I$, $^{125}I$, and combinations thereof.

In operation, the particle suspension is formed by preparing the particle precursor solution of cation (in our examples, yttrium) salt and sodium phosphate to define an admixture. The admixture is then mixed and heated to yield a plurality of $YPO_4$ particles by controlled precipitation. The resulting $YPO_4$ particles are rinsed (typically multiple times, more typically three times) with a sterile phosphate buffered saline (PBS) solution and removing or adding PBS to achieve the final desired volume. The pH of the final solution is adjusted, such as by the addition of sodium hydroxide or the like, and then any excess solution is removed or sterile PBS is added to achieve a final desired volume. The $YPO_4$ particles are then suspended in a phosphate buffered saline solution at neutral pH, suitable for injection in vivo into human or animal tissue.

The yttrium phosphate particles are radioactive so as to serve as distributed sources of therapeutic radiation for treating cancerous tumors and other diseases, such as by adding a predetermined amount of soluble radioactive $^{90}Y$ isotope to the particle precursor solution, that becomes homogeneously incorporated into the insoluble yttrium phosphate particle matrix, solubility of less than about 10-6 mole/liter, more typically less than $10^{-27}$ Ksp. The amount of radioactive yttrium (or like cation) is typically from about 100 uCi to 300 mCi; the specific amount needed varies for each patient application, Typically, the yttrium phosphate particle suspension has $YPO_4$ particle concentration in the range of 40 mg/ml to 125 mg/ml to facilitate imaging by x-ray computed tomography after being combined in a ratio of about 1 to 4 to 1 to 10 by volume with biocompatible hydrogel or other suitable liquid carrier solution for injection into human or animal tissue. Again, while the above example focusses on the yttrium cation, the technique may be adapted to accommodate others of the radioisotopes of interest.

It is well known in radiomedicine that certain types of cancerous tumors may be treated by the localized introduction of short-lived radioisotopes at the tumor site. One effective method of delivering such a radiation treatment is by introducing radioisotopes to the tumor site that emit gamma or beta radiation at therapeutic levels and intensities and that are suspended or otherwise contained in a thermal gel matrix, the gel being a liquid at room temperature that forms a solid gel upon warming to internal body temperature. The $^{90}Y$ or like radiotherapeutic radionuclide is typically introduced in the form of an insoluble stable oxide, phosphate, or the like, and suspended or dispersed in the thermal gel precursor, shortly before introduction into the patient's system. Typically, the predetermined radiotherapy treatment element has a short half-life, so that the radiation treatment is relatively short in duration; more typically, the predetermined element is selected such that it emits relatively high energy beta particles and/or alpha particles and/or gamma rays. For example, $^{90}$Y has a half-life of 64 hours and emits beta particles with a mean energy of about 930 keV. This technique enjoys the advantage of using a thermally setting gel matrix prepared from stable, non-radioactive materials; the non-radioactive thermal gel may be safely stored for an indefinite period and combined with yttrium-90 or a like radiotherapy treatment element shortly before introduction into a patient's body.

Other potential radioisotopes that may be introduced via the thermal gel matrix include $^{131}$Cs, $^{125}$I, $^{121}$TE, $^{103}$Pd, $^{117m}$Sn, and the like, which emit an Auger x-ray upon decay, and beta or beta/gamma emitters such as $^{32}$P, $^{67}$Cu, $^{127}$Te, $^{131}$I, $^{177}$Lu, $^{186}$Re, $^{188}$Re, and the like. In operation, Cs-131, I-131 and/or I-125 and the like may be incorporated into the cage structure of sodalite to yield an insoluble cesium sodalite compound, for example (such as via the hydrothermal synthesis of sodalite with Cs substituting for Na and/or I substituting for Cl in the crystal structure); likewise, Sn-117m may be incorporated as an insoluble Sn apatite compound.

Still other potential radioisotopes that may be introduced via the thermal gel matrix include alpha-particle emitters such as $^{212}$Pb, $^{223}$Ra, $^{225}$Ac, their respective decay products, and the like. These materials tend to form insoluble or sparingly soluble phosphates, and are thus good candidates for the novel treatments and materials described herein.

Radiomedicine thermal gels, such as those containing radioactive $^{90}$Y, emit a therapeutic intensity and amount of short-range beta radiation that can penetrate tissue to a depth of several millimeters. $^{90}$Y is a commonly used radiotherapeutic isotope. $^{90}$Y is a high-energy beta-emitting isotope with no primary gamma; the maximum energy of the $^{90}$Y beta particle is 2.28 MeV with a mean energy of about 0.93 MeV. $^{90}$Y has a half-life ($t_{1/2}$) of 64 hours, with 94% of its radiation delivered in approximately 11 days. Typically, the concentration of radioisotope in the thermal gel and the amount of thermal gel introduced into a patient is controlled such that they will not emit an excess amount of unwanted beta or gamma radiation that could damage healthy tissue surrounding the target tumor. Thus, the thermal gel composition is typically engineered so that the therapeutic radioisotopes are the only constituent isotopes which emit a significant amount of alpha, beta and/or gamma radiation, and that the radioisotopes have a sufficiently short half-life that the radiation emissions are extinguished after a relatively short period of time, typically on the order of several days to a few months. Elements such as yttrium and phosphorus which form radioisotopes having a half-life greater than about two days and less than about 30 days are typically chosen as the constituent elements which are induced to emit therapeutic radiation.

The radiomedicine thermal gels discussed above are thus designed to emit high energy beta particles and/or alpha particles and/or gamma rays that have a relatively short penetration depth in tissue. While this is desired insofar as it optimizes tumor treatment while minimizing collateral tissue damage, it does pose a detection issue. Thus, it is advantageous to in certain instances introduce a second quantity of radioisotope characterized by emissions compatible with SPECT or PET techniques that facilitate PET or SPECT imaging of the radiation distribution patterns in the patient and also aid in imaging of where the thermal gels deposit to ensure uniform deposition in and around the tumor site.

As with the treatment thermal gel, the composition of the imaging agent is selected such that the thermal gel emits a sufficient amount of positron emissions to facilitate PET imaging. In other words, the composition of the imaging agent is typically chosen so that its radiation may be tailored to deliver a radiation profile that is well suited for a particular imaging technique. For instance, when desired for use with PET imaging, the imaging thermal gel will typically include a short-lived positron emitter, such as $^{64}$Cu (half-life of 12.7 hours) or $^{18}$F (half-life of 110 minutes) or the like. $^{64}$Cu and $^{18}$F are particularly attractive positron emitters, as they have short half-lives and emit low energy positrons that annihilate with electrons to produce two 511 keV gammas, which facilitates PET imaging. If longer-lived positron emitters are desired, $^{89}$Zr (half-life of 78.4 hours) or $^{124}$I (half-life of 4.18 days) or the like may be selected.

In most instances, it is desirable to use a thermogel incorporating both treatment radioisotopes and imaging radioisotopes, such as a positron emitter (like $^{64}$Cu) along with a beta and gamma emitter (like $^{86}$Y) or a high-energy beta emitter (like $^{90}$Y), such that the therapeutic treatment thermogel may themselves be directly imaged and tracked. In one such embodiment, a beta emitter and/or a low energy gamma emitting nuclide is incorporated along with a positron emitter into the thermogel The treatment and imaging thermogel is typically introduced into the patient's body via catheter, injection or the like, gelation rapidly occurs in vivo, and the gel becomes lodged in the cancerous or tumor bearing tissue. The treatment and imaging thermogel is typically introduced as a liquid medium of sufficient density and viscosity such that the thermogel remains liquid during the administration procedure and gels rapidly upon introduction into the relatively warm target tissue.

The thermal gel has a composition that becomes more viscous when warmed to a higher temperature. Typically, thermal gel is more fluid at room temperatures and gels to become substantially more viscous, essentially behaving as a solid, at temperatures experienced in vivo. In one embodiment, a PLGA-g-PEG polymer was synthesized having a gelation temperature in phosphate buffered saline (PBS) of 26° C. Several batches of polymer were synthesized in order to narrow the conditions necessary to obtain a gelation temperature around 26° C. The reaction conditions, polymer composition from NMR, and gelation properties from dynamic rheology are summarized below in Table 1. The rheology data for the 30 w % polymers in PBS is shown below.

TABLE 1

| Polymer | EPEG (g) | MPEG (g) | Reaction T (° C.) | Cleaning | NMR LA/GA/EG | Tgel | G' at 37° C. (Pa) | G" at 37° C. (Pa) |
|---|---|---|---|---|---|---|---|---|
| AMIC1 | 39.75 | 3.375 | 121.6 | 2X | 3.17/1/3.20 | 21.9 | 9.83 | 31.69 |
| AMIC2 | 48.00 | 5.184 | 120.25 | 2X | 3.15/1/3.36 | 23.8 | 17.3 | 39.9 |
| AMIC3 | 48.00 | 5.184 | 119.90 | 1X | | 27.3 | 1.11 | 9.84 |

Example

A quantity of thermal gel was prepared according to the above recipe given for AMIC 1. The EPEG referenced in Table 1 was the specific precursor catalog item from Polysciences, EPEG 600, referred to in the prior art. Subcontract laboratory, IsoTherapeutics Group (ITG), of Angleton, TX ran tests to replicate the polymer described in AMIC1. Their testing is summarized below.

It is apparent that the results were not fully reproducible from one lab to another in terms of gelation temperature, MW, LA/GA/EG ratios, and overall polymer yield. Subsequent work at other contract laboratories indicated further differences in polymer characteristics and overall yield from the same starting recipe. Subject matter experts noted that use of EPEG as a thermo-gelling polymer precursor was unusual and that it is not clear that the idealized polymer structure presented in the prior art and subsequently

| Run | Date, End of Run | EPEG, g | MPEG, g | LA, g | GA, g | Toluene, mL* | Reaction T, °C | Tmax, °C | Time, hr | Color (polymer) | Gel T, °C | Time to gel, 37 C. | NMR, LA:GA:EG | MW, HPLC | Polymer Yield, g |
|---|---|---|---|---|---|---|---|---|---|---|---|---|---|---|---|
| AMIC1 | Oct. 22, 2015 | 40 | 3.5 | 35 | 8.75 | 25 | 117-121 | 121 | 17.75 | Dark orange | 25 | | 3.03:1:2.05 | 4913 | |
| AMIC2 | Nov. 25, 2015 | 48.4 | 5.25 | 35 | 8.7 | 20 | 125-121 | 125 | 17.25 | Dark orange | No gel | | 3.17:1:5.22 | | |
| AMIC2A | Dec. 10, 2015 | | | | | | | | | | No gel | | 2.99:1:4.00 | | |
| AMIC3 | Dec. 18, 2015 | 44 | 4.2 | 35 | 8.75 | 30 | 125 | 130 | 18.5 | Dark orange | 35 | | 3.22:1:4.08 | | |
| "AMIC0" | Jan. 14, 2016 | 41 | 3.75 | 35 | 8.75 | 10 | 120 | 200 | 18 | Brown-black | N/A | | | | |
| AMIC4 | Jan. 22, 2016 | 41 | 8.7 | 35 | 8.75 | 0 | 120-122 | 140 | 16 | Dark brown | No gel | | | | |
| AMIC5 | Jan. 27, 2016 | 41 | 3.75 | 35 | 8.75 | 10 | 114 | 114 | 17.5 | Light orange | 25 | | 3.07:1:2.81 | 4481 | |
| AMIC6 | Jan. 29, 2016 | 41 | 3.75 | 35 | 8.75 | 5 | 118 | 118 | 16.5 | Orange | 25 | | 3.10:1:2.82 | 4592 | |
| AMIC7 | Feb. 29, 2016 | 41 | 3.75 | 35 | 8.75 | 20 | 115-118 | 118 | 20 | Light orange | N/A | | 2.84:1:1.64 | | |
| AMIC8 | Mar. 4, 2016 | 41 | 3.75 | 35 | 8.75 | 10 | 115-122 | 128 | 19 | Dark orange | 38 | | | | |
| AMIC9 | Mar. 11, 2016 | 41 | 3.75 | 35 | 8.75 | 10 | 113-118 | 121 | 18.75 | Brown-black | No gel | | | | |
| AMIC10 | Mar. 18, 2016 | 40 | 3.5 | 35 | 8.75 | 20 | 115-127 | 127 | 19 | Dark brown | No gel | | | | |
| AMIC11 | Mar. 30, 2016 | 40 | 3.5 | 35 | 8.75 | 31 | 113.5 | 113.5 | 17 | Straw yellow | 24 | 30 s | 2.99:1:2.28 | 4298 | 35.81 |
| AMIC12 | Apr. 4, 2016 | 40 | 3.49 | 35.01 | 8.75 | 31 | 114 | 115 | 17 | Dark yellow | 23 | 30 s | 3.08:1:2.25 | 4440 | 41.12 |

Other

Only one CH2Cl2/Ether cycle; max viscosity at 38 C., but no gelling

Max viscosity at 39, no real gel; prepared by re-dissolving AMIC2 and extracting one more time Disposed of product w/o gel workup Difficult to control T; no gelation 23-40 C.; polymer gave hard pot on either addition, though did dissolve in CH2Cl2 for further extractions; dissolved in PBS Lots of toluene reflux during heating probably kept T down Did not dissolve in PBS, NMR shows low EG incorporation Used Arpurge instead of N2 during GA, LA, Sn addition. No gelation 21-40 C.; polymer gave hard ppton ether addition, though did dissolve in CH2Cl2 for further extractions, dissolved in PBS, took samoles at 1.25, 4.0, 8.5 and 18.75 hr Polymer behaved better during process that AMIC9, and was slightly better colored (transparent, though dark brown)

Dissolution in PBS took longer than usual(~24 hrs); reaction carried out under nitrogen Dissolution in PBS took longer than usual(~24 hrs); reaction carried out under nitrogen

*Note: runs (AMIC1-10) start with 150 mL toluene, of which 100 mL is distilled off. Sn is added with 5 mL toluene. These 55 mL are not included in this column, only later addition

*Note: runs (AMC11-12) start with 110 mL toluene, of which 20 mL is distilled off. Sn is added with 5 mL toluene. LA/GA added with 5 mL of toluene. These 90 mL are not included in this column, only later addition

| Chemicals | | | Lot |
|---|---|---|---|
| EPEG | Polysciences | 08211 | 550660 |
| MPEG | Polysciences | 04457 | 576039 |
| Lactide | Polysciences | 16640 | 686032 |
| Glycolide | Polysciences | 17085 | 671734 |
| Sn Octoate | Aldrich 53252 | | SLBM6601V |
| Toluene | Aldrich 244511 | | SHBG3513V (AMIC1-10); SHBG6570V (AMIC11-12) |
| Ether | Aldrich 309966 | | SHBG4763V; SHBG6647V | described in the technical literature is achieved using this method. It is likely, due to the bi-functional structure of the EPEG, that having two reactive epoxy ends to each PEG molecule facilitates cross-linking within and between the polymer chains that can strongly influence both the aqueous solubility and gelation properties of the polymer.

Various reaction parameters were tested but it was quickly realized that rigorous steps were needed to assure reaction conditions that were completely water and oxygen-free to avoid deleterious side effects. Applying such techniques allowed an increase in reaction temperature and ability to achieve high reaction yield (~90%) vs. prior yields of <50%. Examining the reaction stoichiometry illuminated that the previous recipe transferred from the prior art relied upon supplying EPEG in excess and controlling specific reaction conditions to achieve the desired product and was not robust or highly reproducible in producing the desired product.

An example of a composition using different molecular weights and stoichiometric ratios of starting components that would yield desirable gelation characteristics is as follows:

| 210719 | mass | MW | Mole | n | mole | Ratio | EPEG/MPEG | mPEG 750, reduced EG-repeat of 0628 |
|---|---|---|---|---|---|---|---|---|
| EPEG | 30 | 536 | 0.0560 | 9.23 | 0.5165 | 3.331 | 8.57 | Aldrich 475696 Acros |
| MPEG | 3.5 | 750 | 0.0047 | 16.32 | 0.0762 | 0.491 | | 192325000 |
| Lactide | 35 | 144.1 | 0.2429 | 2 | 0.4858 | 3.133 | | |
| Glycolide | 9 | 116.1 | 0.0775 | 2 | 0.1550 | 1.000 | | |
| Sn-oct | 0.5 | 405 | 0.0012 | | | | | |
| Sn | 0.147 | | | | | | | |

The prior art does not teach the importance of solvent selection and method of purifying the final polymer. It was found that type of organic solvent, relative volume, and number of dissolution/precipitation cycles was important to achieving the desired end properties. This is attributed to the observation that these cycles remove lower molecular weight fractions of incompletely polymerized material. However, having a portion of those materials present in the final mixture helps achieve the desired gelation properties. Further, it is desirable to select solvents with properties of low toxicity and ease of removal from the final polymer mixture. This is to assure residual levels of solvents in the final product will meet FDA guidelines for allowable concentrations of solvents in medical products for injection. Solvents may be removed by applying heat and high vacuum, freeze drying, etc. but the rigor of conditions required to meet limits can be optimized through choice of solvent and purification conditions.

Ultimately the polymer must be dissolved in aqueous media to be suitable for injection into the body and to achieve the desired gelation properties, such as gelation temperature and gel strength as measured by rheological parameters. It is a balance between low viscosity at room temperature for ease of handling and loading into needles and the temperature range in which the gel forms and the ultimate strength of the gel. It is commonly assumed with this class of polymers that dissolution in phosphate buffered saline is adequate to achieve physiological pH of 7.4. However, it was discovered that the standard buffer is inadequate yielding much lower pH levels. By tailoring the concentrations of inorganic buffer ions, we were able to achieve neutral pH. This might also be achieved with certain organic buffer solutions. We discovered that buffering also changed the rheological properties significantly allowing gelation over a wider temperature range and ultimately higher strength of the final gel.

The above-noted prior art teaches that certain combinations of thermogelling polymer solutions can provide desired properties such as gelation temperature, gel strength, and also tailoring of the time required for the polymer to degrade into fragments that can be resorbed in the body. Combinations of different thermogel types to achieve desired properties are not known a priori. Synergistic effects, or conversely antagonism or deactivation of function, are not obvious by analysis of theoretical polymer structure. The combination of radioactive particles with various thermogelling hydrogel compositions to achieve well-dispersed sources of radioactivity when injected or placed in tissue are likewise not inherently obvious. We have examined the utility of combining radioactive particles with various available thermogelling polymers and combinations to achieve desired properties for both interstitial injection as a dispersed source of therapeutic radiation as well as bolus or planar sources of therapeutic radiation.

Example

Approximately 80 mL anhydrous toluene was measured into a 100 mL volumetric flask using the following procedure: the flask was sealed with a rubber septum and vacuum purged using an 18 G needle attached to a rubber hose. When negative pressure was achieved, the needle was removed. One end of a 24 inch double sided 20 G cannula needle was inserted through the septa-seal all the way to the bottom of a bottle of anhydrous toluene. The other end of the cannula was inserted into the rubber septum of the volumetric flask. Argon was pumped into the bottle of toluene using the 18 G needle attached to the rubber hose, causing the toluene to be transferred into the flask without coming into contact with air or moisture. The flask was filled to ~80% capacity, for a total of approximately 80 mL of anhydrous toluene.

An acetone rinsed, 100 C dried, desiccator cooled 2-neck 500 mL round bottom flask (RBF) with magnetic stir bar was tared. 30.01 g EPEG was slowly pipetted in. The RBF was tared again. 3.51 g mPEG 750 was added into the RBF. Added ~80 ml toluene to the flask. An argon hose was connected to a stopcock attached to the side neck of the RBF and argon was gently pushed through the system (~40 cc/min) while a vacuum distillation apparatus was assembled. A distillation head was connected to the center neck. Set the condenser temperature on a water-recirculator to −10° C. A 250 mL 1-neck RBF along with a condenser drip-tip plus barbed side arm was attached to the end of the condenser head. The argon line was removed from the stopcock and attached to the barb on the drip-tip adapter; the stopcock was left open to vent argon. Ice-packs were packed around the 1-neck RBF collector. The argon was turned off and the stopcock was closed. Vacuum was applied through the hose attached to the drip-tip adapter. The PEG/Toluene solution was set to stir ~200 RPM at SoC. In this manner, the PEGs were vacuum distilled until the toluene appeared to be gone (~1 hour). Afterward, the heat was turned off and the system was allowed to cool to room temperature under continuous vacuum. Once cooled, the system was backflushed with argon. Once pressure inside the system had equalized, the stopcock was opened to facilitate ventilation. Under continuous (~100 cc/min) argon flow, the distillation assembly was removed keeping the stopcock in the side neck. Argon flow was slowed to ~25 cc/min. Through a funnel in the center neck, added 35.01 g D,L-Lactide and 9.01 g Glycolide. Pipetted in 5.0 mL of a 10% Sn octanoate/Toluene (w:v) solution. The center neck was sealed with a glass stopper and the reaction flask was vacuum purged for ~1 hour followed by argon backflush. Through a funnel in the center neck, added ~100 mL anhydrous toluene (drawn from the bottle in the same manner as before). The stopcock was moved to the center neck. A 9" glass Pasteur pipette was pushed through a thermometer adapter which was attached to the side neck, so that the tip of the pipette penetrated to ~1.5 inches below the surface of the reaction solution. Pumped a slow flow of argon through the pipette (~50 cc/min) with 300 RPM stirring for ~20 minutes. A reflux condenser topped with a dry-trap was attached to the center neck. Coolant was circulated through the condenser at −10 C. The stopcock was moved to the side neck, and argon was pumped in through the stopcock at ~50 cc/min for ~30 minutes. The stopcock was closed off and the heat was set to 130° C. for 24 hours with 300 RPM stirring. Next day, the reaction solution was rotary-evaporated until all toluene appeared to be gone. 250 mL acetone was used to re-dissolve the polymer. 155 grams of elutriated activated granulated charcoal (~2× mass) was measured into a 1 L bottle, then the polymer solution was poured over top of the activated charcoal, whereupon tin was substantially removed. Acetone was used to rinse residual polymer from the reaction flask into the bottle. The bottle was capped and left to sit, stationary, in a desiccator chamber overnight. The solution was then pulled through a buchner funnel with moderate vacuum; copious acetone was used to rinse as much polymer as possible from the granulated carbon. The filtrate was passed through a series of poly-vinylidine fluoride (PVDF) filters, finishing with a 0.1 um pore size membrane. The filtrate was transferred into a 1 L pear-shaped flask and rotary-evaporated to approximately 200 mL, then it was poured directly into 2 L stirring hexane. The precipitated material was collected and dried under vacuum at 55° C., giving about 85% yield, with less than 65 ppm residual tin.

The monomer ratio was optimized for gelation properties. The table below provides the analysis specifications for this Example.

| Test | Test Method | Specification | Sample Size |
| --- | --- | --- | --- |
| Color | Visual | Clear to straw-colored liquid (Inspect prior to labeling) | 100% of Lot |
| Foreign Particulate Matter | Visual | No Visible Particles (Inspect prior to labeling) | 100% of Lot |
| Tip Test | Place 30% polymer 70% Phosphate Buffered Saline in a thin walled glass container. Place in a heat block or water bath at 35° C. Invert every 30 seconds until gel forms. | Polymer/PBS mixture gels and will remain in place during tip test. | 0.2-2 mL of Lot as hydrogel |
| PLGA-g-PEG content | NMR (Nuclear Magnetic Resonance) Spectroscopy | LA:GA:EG ratio 3.0:1:3.3 (Range LA 2.9-3.1; EG 2.5-4.1) | 5-10 mg |
| Rheology G' (Storage)/G" (Loss) Modulus | 30 wt % polymer in phosphate buffered saline. Cone and plate rheometry. | Oscillation constant of 6.283 rad/s; 0.1% strain, increments of 1° C., 5 to 45° C. with 1 minute of temperature equilibrium at each point. Report viscosity (Pa-s) at 5° C., maximum G' and G" (Pa), and temperature (° C.) of onset of increase in G' and G". Typical ranges; G' values 6 to 15, G" values 16 to 46, crossover from 31° C. to 39° C. | 3 to 5 mL as hydrogel |
| Average Molecular Weight | Gel Permeation Chromatography | 4200-5600 Da (Mw) with a PDI of 1.5-2.0 | |
| Lot Number | Visual | Correct and Legible Lot Number per Production Order | 100% of Lot |
| Expiration Date | Visual | Correct and Legible Expiration Date; The expiration date must be 90 days from the date of completion of manufacture. | 100% of Lot |

In general, the PLGA-g-PEG gel material so produced enjoys selective optimization of the monomer ratios presented to achieve optimal gel property formation in a highly reproducible manner. The reaction is conducted under selective conditions for maximum removal of oxygen and water molecules from the reactive solution prior to initiation, which is counter-intuitive to prior efforts in this area. Purification is accomplished via combination of hexane-based non-solvent precipitation and removal of stannous octanoate via activated charcoal soak followed by filtration, without the need for multiple washes to achieve desired gelation characteristics. The removal of tin from the gel renders the gel more biocompatible.

Numerous radioactive isotopes are suitable for delivery of therapeutic radiation to diseased or unwanted tissue or for external imaging of source placement or both. Various physical and chemical forms are described including insoluble inorganic compounds, organic chelating/complexing agents, or encapsulation in inert media such as glass microspheres. The specific method of immobilization necessarily depends on the chemical properties of the desired isotope and the degree of immobilization needed in the in-vivo environment. We have developed novel means of immobilizing isotopes such as P-32, P-33, Re-186, Re-188, Lu-177, Sm-153, Sn-117m, Cs-131, Pd-103, Cu-64, Cu-67, and others. These embodiments are specifically designed to be compatible with PLGA-g-PEG and other hydrogels and combinations of hydrogels to provide localized sources for in-vivo treatment of cancer and other disease.

One advantage of the novel thermogel and thermogelling methods disclosed herein is the ability to utilize additives with radioactive sources in thermogelling hydrogel carriers for various purposes. Additives considered include analgesics, anti-cancer agents, antibiotics, imaging agents, combinations thereof, and the like. We have evaluated the utility of incorporating such agents, in particular use of antibiotics to counter the potential for infection to develop at the site of administration of radioactive source material. An interesting parameter in this regard is the resistance of such agents to degradation by exposure to radiation and ability to retain their desired function. Also of interest is the absence of deleterious degradation products to assure safety of use.

Example

In this example, all samples were reconstituted at a concentration of 31.25% w:v hydrogel solutions in phosphate buffered saline (PBS) at cold temperature. All three solutions were kept refrigerated.

Under a laminar flow hood, 8 mL of the PLGA-g-PEG and AK097 solutions were injected into separate vials containing $YPO_4$ particles with each vial containing ~1 mL $YPO_4$ particles (~59 mg/vial)). 1 mL 0.2 um filtered PBS was injected into each of the hydrogel/YPO4 solution vials. The vials were vortexed for ~10 seconds each. The vials were stored in the refrigerator while the next solution was prepared.

Under a laminar flow hood, 9 mL of the Pluronic F-127 solution was injected into a vial containing ~1 mL $YPO_4$ particles. The vial was vortexed for ~10 seconds. 5.0 mL of each solution was transferred into 50 mL Falcon tubes (previously warmed to 37 C). The tubes were held static in a 37 C incubator until gelled. 5 mL of 37° C. PBS was pipetted into each tube. The tubes were held at 37° C. with 100 RPM shaking for 10 minutes. 4 mL of supernatant from each tube was transferred into vials and subjected to yttrium analysis, yielding the following values for yttrium in the supernatant. Note that this indicates yttrium which was not successfully entrapped.

| Name | Identifier (MFG, cat#) | Yttrium in supernatant (ppm) |
|---|---|---|
| Poly(lactide-co-glycolide)-b-Poly(ethylene glycol)-b-Poly(lactide-co-glycolide) (Mw~1700-1500-1700 Da) LA:GA 15:1 | PLGA-PEG-PLGA, (Akina, Inc. Cat# AK097) | <5.0 |
| polyethylene glycol-b-polypropylene glycol (Mw~12600 Da) | Pluronic F127 (Aldrich Cat# P2443) | 227 |

-continued

| Name | Identifier (MFG, cat#) | Yttrium in supernatant (ppm) |
|---|---|---|
| Poly(lactide-co-glycolide)-graft-Poly(ethylene glycol) | PLGA-g-PEG (lot# 211011RAI-A157) | <5.0 |

The use of a thermogel to entrap and isolate yttrium particles is non-obvious as not all thermogels work for this application. Notably Pluronic F127 failed to entrap these particles. Although both PLGA-PEG-PLGA (triblock) and PLGA-g-PEG successfully entrapped the particles; the PLGA-g-PEG has advantages over PLGA-PEG-PLGA in other properties including reconstitution speed and ease of handling.

Example

Preparation of insoluble or sparingly soluble particles that incorporate radioactive palladium-103 ($^{103}Pd$) as the source of therapeutic radiation. $^{103}Pd$ emits low energy x-rays (photons) with an average energy of about 22 KeV that may be attenuated only a few centimeters in soft tissues. A therapeutic dose can be delivered by administering in the range of 3.5 mCi per $cm^3$ of tumor or cancerous tissue. Due the high specific activity of $^{103}Pd$, only a small mass on the order of one microgram of $^{103}Pd$ would be needed to effectively treat a typical 30 $cm^3$ size tumor. As palladium is a rare and expensive element, it is advantageous to take advantage of its specific chemical properties to form insoluble or sparingly soluble particles that incorporate radioactive $^{103}Pd$ species within, or adhered to, a chemically inert particle matrix. In one embodiment, $^{103}Pd$ metal is galvanically or electrochemically plated onto a less expensive substrate, such as copper, silicon, or alumina. In another embodiment, soluble palladium chloride is deposited onto an inert substrate such as alumina or silica, and the resulting compound is heated to yield palladium oxide and/or reduced to yield palladium metal. In yet another embodiment, an insoluble palladium compound, such as palladium thiocyanide ($Ksp=4\times10^{-23}$), is formed with or coated onto a non-radioactive compound (such as copper thiocyanide) yielding palladium radionuclide coated inert microspheres of a desired particle size range. In still another embodiment, the palladium radionuclide is isolated as an iodide, which is insoluble or sparingly soluble in water, alcohol, and ether. Alternately, the palladium radionuclide may be isolated as an insoluble hydride or simply reduced to a zero-valence metal.

After the isotope is isolated, it is combined with the gel as described above and administered to the tumor site. A further advantage of forming such $^{103}Pd$ bearing particles beyond the use of lower cost materials is to use compounds and alloys of lower density than palladium to reduce self-shielding of the low energy photons that are emitted thereby improving the efficiency of utilization of the radioactive isotope for radiation therapy.

Example

Other isotopes of interest include alpha emitters such as actinium-225 ($^{225}Ac$). Alpha particles travel short distances in tissue yet still transit several cell diameters from the source, in the range of 40 to 90 microns. Dispersing micron-sized particles throughout the interstitial space within tumor tissue can deliver a highly effective dose of localized radiation with virtually no exposure to adjacent normal tissues. Forming an insoluble or sparingly soluble particle incorporating radioactive $^{225}$Ac can be achieved by taking advantage of its chemical properties. Actinium forms very low solubility phosphate compounds, similar to the Lanthanides but only a very small mass of radioactive $^{225}$Ac is needed to deliver a therapeutically effective dose. Thus, it is advantageous to combine the radioactive $^{225}$Ac with other insoluble but non-radioactive phosphate compounds to achieve particles of sufficient mass for brachytherapy or like radiotherapy treatment. Examples of such compounds include yttrium phosphate, copper phosphate, barium phosphate, combinations thereof, and the like. An advantage of combining actinium phosphate with barium phosphate is that barium is highly visible in x-ray imaging and sufficient barium content could allow imaging the radioactive particles using multi-planar x-ray or x-ray computed tomography (CT). Yet another advantage of encapsulating and immobilizing the $^{225}$Ac (or like radionuclide, such as uranium, cesium, technetium, tin, and the like) within an inert particle (such as extremely biocompatible apatite, sodalite, tricalcium phosphate, or the like), or as a coating on another inert particle, is the ability to retain alpha particle emitting daughter products of $^{225}$Ac of which there are several distinct daughters in the $^{225}$Ac decay chain. Traditional chelation chemistry is not fully optimized to retain all of the daughters in the decay scheme as their chemistry changes as they transition through the decay chain daughter isotopes. Encapsulating the parent isotope $^{225}$Ac in an insoluble chemical matrix minimizes the potential for the daughter isotopes to escape and migrate away from the treatment site. After the isotope is isolated, it is combined with the gel as described above and administered to the tumor site.

While the invention has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the invention are desired to be protected.

We claim:
1. A radioactive thermogel suspension, comprising:
   a thermogel; and
   a plurality of radioactive yttrium phosphate particles suspended in the thermogel;
   wherein the thermogel comprises a PLGA-g-PEG polymer prepared substantially free of water molecules and oxygen molecules dissolved in an aqueous buffer solution;
   wherein the plurality of radioactive yttrium phosphate particles are between 0.03 μm and 10 μm diameter;
   wherein the plurality of radioactive yttrium phosphate particles are generally spherical; and
   wherein the YPO$_4$ particle concentration is in the range of 3 mg/ml to 100 mg/ml.

2. (The radioactive thermogel suspension of claim 1 wherein the radioactive yttrium phosphate is combined with the thermogel to yield a final concentration of thermogelling polymer in the range of about 25 w % to 30 w % in aqueous buffer solution.

3. The radioactive thermogel suspension of claim 1 wherein the radioactive thermogel suspension has a pH between 1.5 and 8.0.

4. The radioactive yttrium phosphate suspension of claim 1 wherein at least some of
   the yttrium phosphate includes a radioactive phosphorus isotope.

5. A radioactive thermogel suspension, comprising:
   a thermogel, wherein the thermogel comprises a PLGA-g-PEG polymer which is prepared substantially free of water molecules and oxygen molecules dissolved in aqueous buffer solution; and
   a plurality of chemically isolated radioactive particles suspended in the thermogel, wherein each chemically isolated radioactive particle includes a cation and a functional group; and
   wherein the plurality of chemically isolated radioactive particles are between 0.03 μm and 10 μm in diameter.

6. The radioactive thermogel suspension of claim 5 wherein the plurality of chemically isolated radioactive phosphate particles are between 0.1 μm and 2 μm in diameter.

7. The radioactive thermogel suspension of claim 5 wherein the chemically isolated radioactive particles have solubility of less than $1 \times 10^{-6}$ mole/liter.

8. The radioactive thermogel suspension of claim 5 wherein the cations are selected from the group consisting of Y, Ho, Yb, Ce, Pb, Pd, Cs, Ac, Sm, Lu, Sc, Ca, Sr, Ba, and combinations thereof.

9. The radioactive thermogel suspension of claim 5 wherein the functional group includes isotopes selected from the group consisting of $^{31}$P, $^{32}$P, $^{33}$P, $^{123}$I, $^{124}$I, $^{125}$I, and combinations thereof.

10. The radioactive thermogel suspension of claim 5 wherein the chemically isolated radioactive particle concentration is in the range of 3 mg/ml to 100 mg/ml.

11. The radioactive thermogel suspension of claim 10 wherein the chemically isolated radioactive particles provide a dosage of between 100 μCi and 300 mCi.

12. The radioactive thermogel suspension of claim 5 wherein the cations are selected from the group consisting of Y, La, Ce, Pr, Pm, Sm, Gd, Tb, Ho, Yb, Ce, Pb, Lu, Ac, Ca, Sr, Ba, Ra, Cu, Tc, Pd, Sn, Re, Au, and combinations thereof, and wherein the functional group includes phosphorous isotopes selected from the group consisting of $^{31}$P, $^{32}$P, $^{33}$P, and combinations thereof.

13. The radioactive thermogel suspension of claim 5 wherein the functional group is selected from the group consisting of apatite, sodalite, iodide, hydride, and combinations thereof.

14. A radioactive metal phosphate/thermogel suspension, comprising:
    a PLGA-g-PEG polymer which is prepared substantially free of water molecules and oxygen molecules; and
    a plurality of radioactive metal phosphate particles suspended in a phosphate buffered saline solution, wherein each metal phosphate particle includes a metal cation and a phosphate-bearing functional group;
    wherein the plurality of radioactive metal phosphate particles are between 0.03 μm and 10 μm in diameter;
    wherein the metal phosphate particles are selected from the group consisting of lanthanide phosphates, actinide phosphates, alkali and alkali earth phosphates, transition metal phosphates, and combinations thereof,
    wherein the metal phosphate particles have solubility of less than $1 \times 10^{-6}$ mole/liter;

wherein the phosphate functional group includes phosphorus isotopes selected from the group consisting of $^{31}P$, $^{32}P$, $^{33}P$, and combinations thereof; and
wherein the metal phosphate particles provide a dosage of between 100 µCi and 300 mCi.

15. A radioactive cation-phosphate/thermogel suspension, comprising:
a PLGA-g-PEG polymer which is prepared substantially free of water molecules and oxygen molecules; and
a plurality of radioactive cation-phosphate particles suspended in a phosphate buffered saline solution, wherein each cation-phosphate particle includes a cation and a phosphate-bearing functional group;
wherein the plurality of radioactive cation-phosphate particles are between 0.03 µm and 10 µm in diameter;
wherein the cation-phosphate particles are selected from the group consisting of lanthanide phosphates, actinide phosphates, alkali and alkali earth phosphates, transition metal phosphates, and combinations thereof;
wherein the cation-phosphate particles have solubility of less than $1\times10^{-6}$ mole/liter;
wherein the phosphate functional group includes phosphorus isotopes selected from the group consisting of $^{31}P$, $^{32}P$, $^{33}P$, and combinations thereof;
wherein the cation is selected from the group consisting of Y, La, Ce, Pr, Pm, Sm, Gd, Th, Ho, Yb, Ce, Pb, Lu, Ac, Ca, Sr, Ba, Ra, Cu, Tc, Pd, Sn, Re, Au, and combinations thereof; and
wherein the cation-phosphate particles provide a dosage of between 100 µCi and 300 mCi.

16. A chemically isolated radioactive palladium/thermogel suspension, comprising:
a PLGA-g-PEG polymer which is prepared substantially free of water molecules and oxygen molecules; and
a plurality of chemically isolated radioactive palladium particles suspended in a buffered saline solution, wherein each chemically isolated radioactive palladium particle includes a palladium radionuclide and a functional group;
wherein the plurality of chemically isolated radioactive palladium particles are between 0.03 µm and 10 µm in diameter;
wherein the chemically isolated radioactive palladium and functional group is selected from the group consisting of palladium phosphates, palladium thiocyanate, palladium apatite compounds, palladium sodalite compounds, palladium hydrides, palladium plated metals, palladium coated oxides, palladium coated ceramics, and combinations thereof;
wherein the chemically isolated radioactive palladium particles have solubility of less than $1\times10^{-6}$ mole/liter; and
wherein the chemically isolated radioactive palladium provides a dosage of between 100 µCi and 300 mCi.

17. The chemically isolated radioactive palladium/thermogel suspension of claim 16 wherein the palladium radionuclide is $^{103}Pd$.

* * * * *